United States Patent
Pradeep

(10) Patent No.: US 11,801,004 B2
(45) Date of Patent: Oct. 31, 2023

(54) SYSTEMS, METHODS, AND DEVICES FOR INTRACRANIAL MEASUREMENT, STIMULATION, AND GENERATION OF BRAIN STATE MODELS

(71) Applicant: StimScience Inc., Berekeley, CA (US)

(72) Inventor: Anantha K. Pradeep, Piedmont, CA (US)

(73) Assignee: STIMSCIENCE, INC., Berkeley, CA (US)

( * ) Notice: Subject to any disclaimer, the term of this patent is extended or adjusted under 35 U.S.C. 154(b) by 732 days.

(21) Appl. No.: 16/256,363

(22) Filed: Jan. 24, 2019

(65) Prior Publication Data

US 2019/0150768 A1    May 23, 2019

Related U.S. Application Data

(63) Continuation-in-part of application No. 16/170,675, filed on Oct. 25, 2018, now Pat. No. 11,064,938.

(Continued)

(51) Int. Cl.
*A61B 5/374* (2021.01)
*A61B 5/00* (2006.01)
(Continued)

(52) U.S. Cl.
CPC ............. *A61B 5/374* (2021.01); *A61B 5/24* (2021.01); *A61B 5/316* (2021.01); *A61B 5/369* (2021.01);
(Continued)

(58) Field of Classification Search
CPC ......... A61B 5/0524; A61B 5/24; A61B 5/291; A61B 5/316; A61B 5/369; A61B 5/374;
(Continued)

(56) References Cited

U.S. PATENT DOCUMENTS 7,324,851 B1 * 1/2008 DiLorenzo ........... A61N 1/3605
607/45
9,500,685 B2 * 11/2016 Larsson .................. H02J 3/241
(Continued)

OTHER PUBLICATIONS

Zhaleh Pirzadeh, "Modeling the Interaction between Intracranial Pressure and Cerebral Hemodynamics," Master's Thesis in Biomedical Engineering, Report No. Ex083/2009, 2009, 69 pages.
(Continued)

*Primary Examiner* — Christopher A Flory
(74) *Attorney, Agent, or Firm* — SCHWEGMAN LUNDBERG & WOESSNER, P.A.

(57) ABSTRACT

Provided are systems, methods, and devices for intracranial measurement, stimulation, and generation of brain state models. Systems include a plurality of intracranial electrodes configured to be coupled to a brain of a user. Systems further include an interface configured to obtain measurements from the plurality of intracranial electrodes. Systems include a first processing device including one or more processors configured to generate a plurality of brain state parameters characterizing one or more features of at least one brain state of the user, and a second processing device including one or more processors configured to generate at least one model of the brain of the user based, at least in part, on the plurality of brain state parameters and the measurements. Systems include a controller including one or more processors configured to generate a control signal based on the plurality of brain state parameters and the at least one model.

22 Claims, 5 Drawing Sheets

Related U.S. Application Data

(60) Provisional application No. 62/621,459, filed on Jan. 24, 2018, provisional application No. 62/579,300, filed on Oct. 31, 2017.

(51) Int. Cl.

| | |
|---|---|
| *A61N 1/36* | (2006.01) |
| *G16H 50/50* | (2018.01) |
| *A61B 5/24* | (2021.01) |
| *A61B 5/316* | (2021.01) |
| *A61B 5/369* | (2021.01) |
| *A61N 1/05* | (2006.01) |
| *A61N 2/00* | (2006.01) |
| *A61B 5/291* | (2021.01) |

(52) U.S. Cl.
CPC .......... *A61B 5/4836* (2013.01); *A61B 5/6868* (2013.01); *A61N 1/0529* (2013.01); *A61N 1/36139* (2013.01); *G16H 50/50* (2018.01); *A61B 5/291* (2021.01); *A61N 1/0534* (2013.01); *A61N 1/36082* (2013.01); *A61N 2/006* (2013.01)

(58) Field of Classification Search
CPC .. A61B 5/4836; A61B 5/6868; A61N 1/0529; A61N 1/0534; A61N 1/36082; A61N 1/36139
See application file for complete search history.

(56) References Cited

U.S. PATENT DOCUMENTS

| | | | |
|---|---|---|---|
| 11,064,938 B2 | 7/2021 | Pradeep | |
| 2007/0213786 A1* | 9/2007 | Sackellares | A61N 1/36025 607/45 |
| 2012/0221075 A1* | 8/2012 | Bentwich | G16H 50/30 607/45 |
| 2013/0072810 A1* | 3/2013 | Wingeier | A61B 5/369 600/544 |
| 2014/0052033 A1* | 2/2014 | Lawlis | A61M 21/02 601/47 |
| 2014/0350634 A1* | 11/2014 | Grill | A61N 1/36139 607/45 |
| 2015/0174418 A1* | 6/2015 | Tyler | A61N 1/36025 601/2 |
| 2016/0306942 A1* | 10/2016 | Rapaka | A61B 5/0042 |
| 2017/0113046 A1* | 4/2017 | Fried | A61B 5/4094 |
| 2017/0281086 A1* | 10/2017 | Donaldson | A61B 5/14532 |
| 2018/0093092 A1* | 4/2018 | Howard | G01N 21/1702 |
| 2018/0133504 A1* | 5/2018 | Malchano | A61B 5/16 |
| 2019/0125255 A1 | 5/2019 | Pradeep | |
| 2021/0369194 A1 | 12/2021 | Pradeep | |

OTHER PUBLICATIONS

Chanki Park, et al., "Real-Time Non-Invasive Intracranial State Estimation using Unscented Kalman Filter," bioRxiv preprint first posted online Aug. 27, 2018, 32 pages.
U.S. Appl. No. 16/170,675, Non-Final Rejection, dated Nov. 27, 2020, 8 pgs.
U.S. Appl. No. 16/170,675, Examiner Interview Summary dated Mar. 3, 2021, 2 pgs.
U.S. Appl. No. 16/170,675, Notice of Allowance dated Mar. 31, 2021, 5 pgs.
"U.S. Appl. No. 16/170,675, Response filed Feb. 26, 2021 to Non Final Office Action dated Nov. 27, 2020", 10 pgs.
"U.S. Appl. No. 17/351,416, Preliminary Amendment filed Aug. 20, 2021", 6 pgs.
Galgano, Michael, "Traumatic Brain Injury: Current Treatment Strategies and Future Endeavors", Cell Transplantation 2017, vol. 26(7), (2017), 1118-1130.
Reis, Cesar, "What's New in Traumatic Brain Injury: Update on Tracking, Monitoring and Treatment", Int. J Mol. Sci., 16, (2015), 11903-11965.

* cited by examiner

SYSTEMS, METHODS, AND DEVICES FOR INTRACRANIAL MEASUREMENT, STIMULATION, AND GENERATION OF BRAIN STATE MODELS

CROSS-REFERENCE TO RELATED APPLICATIONS

This application claims priority under 35 U.S.C. § 119(e) to U.S. Provisional Application No. 62/621,459, filed Jan. 24, 2018, and is a continuation-in-part of U.S. application Ser. No. 16/170,675, filed Oct. 25, 2018, which claims the benefit of U.S. Provisional Application No. 62/579,300, filed Oct. 31, 2017, which are incorporated by reference herein in their entirety for all purposes.

TECHNICAL FIELD

The present disclosure relates to mechanisms and processes directed to intracranial measurements associated with brain activity.

BACKGROUND

A human brain may include neurons which exhibit measurable electrical signals when active. Accordingly, various measuring modalities, such as electrodes, may be used to measure such electrical activity. The neural activity of neurons may include many a variety of frequency components. Accordingly, such electrical activity may be measured and represented as a power spectrum in a frequency domain. However, traditional techniques for measuring electrical activity remain limited in their ability to stimulate such neurons, and more specifically, their ability to determine suitable stimulation parameters for stimulation applied to a user's brain.

SUMMARY

Provided are systems, methods, and devices for intracranial measurement, stimulation, and generation of brain state models.

In various embodiments, systems include a plurality of intracranial electrodes configured to be coupled to a brain of a user and configured to obtain a plurality of measurements from the brain of the user. Systems further include an interface configured to obtain the plurality of measurements from at least the plurality of intracranial electrodes. Systems also include a first processing device including one or more processors configured to generate a plurality of brain state parameters characterizing one or more features of at least one brain state of the user, and a second processing device including one or more processors configured to generate at least one model of the brain of the user based, at least in part, on the plurality of brain state parameters and the plurality of measurements. Systems also include a controller including one or more processors configured to generate a control signal based on the plurality of brain state parameters and the at least one model.

This and other embodiments are described further below with reference to the figures.

DETAILED DESCRIPTION OF EXAMPLE EMBODIMENTS

Figure 1:
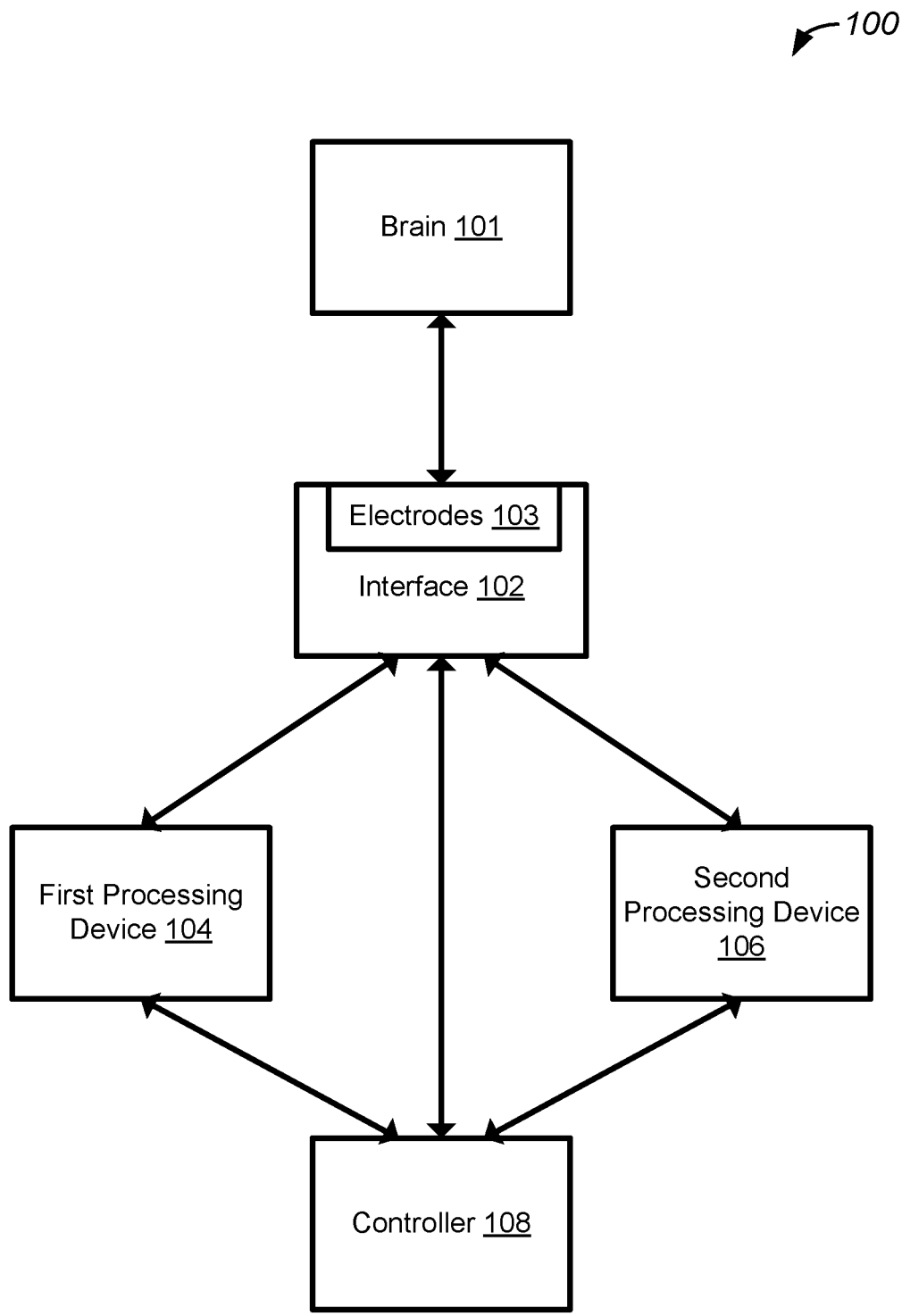
FIG. 1 illustrates an example of a system for providing closed loop control in treatments and cognitive enhancements, configured in accordance with some embodiments.

Reference will now be made in detail to some specific examples of the invention including the best modes contemplated by the inventors for carrying out the invention. Examples of these specific embodiments are illustrated in the accompanying drawings. While the present disclosure is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims. In addition, although many of the components and processes are described below in the singular for convenience, it will be appreciated by one of skill in the art that multiple components and repeated processes can also be used to practice the techniques of the present disclosure.

In the following description, numerous specific details are set forth in order to provide a thorough understanding of the present invention. Particular embodiments of the present invention may be implemented without some or all of these specific details. In other instances, well known process operations have not been described in detail in order not to unnecessarily obscure the present invention.

As discussed above, components, such as electrodes, may be used to measure electrical activity in a brain, as well as provide stimulation to the brain. Traditional techniques remain limited in their ability to stimulate such neurons because they are not able to determine suitable stimulation parameters for stimulation applied to a user's brain. For example, traditional implementations of electrodes might be limited to surface or scalp implementations, and may be limited in sensitivity to signal, spectrum, and localization when obtaining measurements, and determining suitable stimulation protocols, as will be discussed in greater detail below.

Moreover, traditional neuronal signal modeling mechanism have significant limitations. Available brain signal decoding mechanisms only directly measure simple signatures of behavior like the increase or decrease of alpha desynchronization. However, such techniques do not estimate a real state to be modified. For example, alpha desynchrony may just be overall arousal state. Other traditional systems like uni-variate and uni-modal systems are not able to accurately model complicated neural systems. Such simple models do not account for cross impacts of sub-systems or multiple modalities of measurements, and are not able to detect or identify various states or parameters that are to be monitored and controlled. Some other traditional techniques are open loop techniques with electrical or magnetic stimulation of different regions with manual tuning and long term behavior tracking that are not only inefficient but can also be erroneous. Such techniques may result in overstimulation and/or under-stimulation.

As will be discussed in greater detail below, various embodiments disclosed herein provide the ability to obtain measurements and provide stimulation via intracranial modalities, and in conjunction with surface or scalp level modalities. Such intracranial implementations facilitate the measurement and acquisition of electrocortical data, as may be consistent with electrocorticography (ECoG) or intracranial electroencephalography (iEEG), to develop brain state and functional models. The use of such intracranial implementations enables the increase of accuracy of brain state and functional models, as well as the generation and estimation of additional new states that might not be observable and predictable by scalp level modalities alone. Moreover, such intracranial implementations may further enable the increased accuracy of generation of stimulation parameters, such as field strength of actuators as well as a position of actuators.

Various embodiments disclosed herein provide the ability to obtain measurements from a brain of a user, and generate various brain state parameters characterizing one or more features of at least one brain state of the user, as well as various models of the brain of the user. Such brain state parameters implemented in conjunction with the generated models provide a closed loop adaptive therapeutic system that may obtain measurements, generate a generalized or user specific functional and/or structural model of the brain, estimate desired brain signatures and states, generate control signals to obtain such desired brain states, and obtain additional measurements if appropriate to continuously adjust the signals and the models. In this way, various embodiments disclosed herein provide therapeutic and cognitive modulation techniques that are adaptive closed loop techniques that provide, among other things, desired modulations with increased efficiency and efficacy.

As similarly discussed above, at least some of the measurements may be acquired using intracranial data obtained from intracranial electrodes. Such electrodes implanted within the cortical tissue may be configured to have high sensitivity with respect to signal amplitude, frequency spectrum, as well as signal localization. Accordingly, such ECoG data may be utilized to develop and generate brain parameters associated with brain states as well as functional and structural models, as discussed in greater detail below with reference to at least FIGS. 2 and 3. More specifically, the intracranial data be used to generate and identify brain states as well as functional and structural models, and may also be used to generate control signals. Furthermore, such intracranially obtained data may include both normal and pathological episode data thus providing a comprehensive representation of a user's neural activity.

In various embodiments, the use of intracranial data obtained from intracranial electrodes may be co-registered with scalp level measurements and data to improve functional and structural models as well as signature/brain-state estimation. Accordingly, the high sensitivity of the intracranial electrodes may be used to enhance the efficacy and accuracy of such models by providing, among other things, enhanced signal localization relative to portions of the user's brain. In some embodiments, the intracranial data may be used to enhance existing models that were generated based on just scalp level data. In this way, the intracranial data may be used to augment and enhance existing models of a user.

In some embodiments, intracranial implementations disclosed herein are configured to determine region specific field strengths associated with actuators used for stimulation. As discussed above, intracranial electrodes may provide higher sensitivity and greater accuracy regarding the measurement of intracranial data associated with neural activity, as well as the representation of such neural activity in generated functional and structural models. In various embodiments, the intracranial data may be used to determine field strengths and stimulation levels used for actuators, and may also be used to determine suitable positions for such actuators. The use of intracranial data in this manner provides increased accuracy in the determination of the appropriate amount of stimulation to provide by virtue of increased accuracy of the measurements themselves as well as increased accuracy of the models used to determine and generate stimulation parameters. Accordingly, the increased accuracy provided by intracranial implementations disclosed herein reduces the risk of overstimulation of cortical tissue.

Furthermore, intracranial data may be used for forward modeling or estimating states that are not explicitly observable using scalp level modalities. Accordingly, intracranial data may be used to model scalp level data, and estimate or predict observed scalp data. In this way, the intracranial data may be used in conjunction with generated models to predict specific features of scalp level measurements that may otherwise be difficult to observe and identify.

Additional details will be discussed in greater detail below with reference to components of systems disclosed herein as well as brain state and functional model generation, stimulation, closed loop control, and prosthetic control. Accordingly, the implementations of intracranial electrodes discussed above may be implemented in conjunction with systems as disclosed in FIG. 1, and methods as disclosed in FIGS. 2, 3, and 4. For example, such electrodes may be implemented as part of interface 102 discussed in greater detail below, and acquired data may be used in accordance with methods 200, 300, and 400 discussed below.

FIG. 1 illustrates an example of a system for providing closed loop control in treatments and cognitive enhancements, configured in accordance with some embodiments. In some embodiments, system 100 includes an interface, such as interface 102. In various embodiments, interface 102 is a brain interface that is configured to be coupled with a brain, such as brain 101. As will be discussed in greater detail below, such coupling may provide bidirectional communication, or may be used for various sensing modalities. In some embodiments, interface 102 includes various electrodes, such as electrodes 103, which may be included in an electrode array. Such electrodes may be included in a scalp potential electroencephalogram (EEG) array, may be deep brain stimulation (DBS) electrodes such as electrodes used with intracranial electroencephalography, or may be an epidural grid of electrodes. In other examples, interface 102 may include optogenetics mechanisms for monitoring various neuronal processes. Mechanisms may be used to make various measurements and acquire measurement signals corresponding to neural activity. As used herein, neural activity may refer to spiking or non-spiking activity/potentiation.

In various embodiments, such measured signals may be electrical signals derived based on neural activity that may occur in cortical tissue of a brain. Such measurements may be acquired and represented in a time domain and/or frequency domain. In this way, neural activity may be monitored and measured over one or more temporal windows, and such measurements may be stored and utilized by system 100. In various embodiments, such neural activity may be observed for particular regions of cortical tissue determined, at least in part, based on a configuration of interface 102. In one example, this may be determined based on a configuration and location of electrodes included in interface 102 and coupled with the brain.

According to some embodiments, one or more components of interface 102 are configured to provide stimuli to the brain coupled with interface 102. For example, one or more electrodes included in interface 102 may be configured to provide electrical stimuli to cortical tissue of the brain. As discussed above, such electrodes may be implemented utilizing one or more of various modalities which may be placed on a user's scalp, or implanted in the user's brain.

As will be discussed in greater detail below, such actuation and stimuli provided by interface 102 may be of many different modalities. For example, stimuli may be aural, visual, and/or tactile as well as being electrical and/or magnetic, or any suitable combination of these. Accordingly, interface 102 may further includes additional components, such as speakers, lights, display screens, and mechanical actuators that are configured to provide one or more of aural, visual, and/or tactile stimuli to a user. In this way, any suitable combination of different modalities may be used. For example, a combination of electrical and aural stimuli may be provided via interface 102. Further still, interface 102 may include different portions corresponding to signal acquisition and stimuli administration. For example, a first portion of interface 102 may include electrodes configured to measure neural activity, while a second portion of interface 102 includes speakers configured to generate aural stimuli.

In some embodiments, interface 102 further includes one or more dedicated processors and an associated memory configured to obtain and store the measurements acquired at interface 102. In this way, such measurements may be stored and made available to other system components which may be communicatively coupled with interface 102.

System 100 further includes first processing device 104 which is configured to generate brain state parameters that may characterize and identify features of brain states and generate estimations of brain state signatures. In various embodiments, a brain state may refer to one or more identified patterns of neural activity. Accordingly, such brain states may be one or more identified patterns, such as oscillation or fluctuation of activity at a particular frequency band, such as low oscillatory behavior as well as delta, theta, alpha, beta, and gamma waves. Furthermore, such brain states may be identified based on coupling between patterns of neural activity. For example, a brain state may be identified based on oscillation or fluctuation of activity at a particular frequency band, and an increase of activity in another. Other brain states may correspond to phase resets in prefrontal and cingulate areas. Phase resets may correspond to coherent activity in widespread cortical regions and impact timing of neuronal activity. Activity patterns in the prefrontal cortex can be monitored, identified, and controlled for associations with particular behaviors including goal directed behavior. Neuronal synchronization and desynchronization may be detected and managed using closed loop control based on intelligent and continuously adaptive neurological models. As will be discussed in greater detail below, such identification may be implemented based, at least in part, on various parameters, such as observers and estimators.

Accordingly, first processing device 104 is configured to generate one or more particular observers and/or estimators that may form the basis of identification and estimation of brain states, described in greater detail below. As discussed above, first processing device 104 may be configured to generate deterministic and stochastic observers and estimators of brain states based on acquired measurements. Such deterministic observers may provide robustness to exogenous disturbances, while such stochastic estimators may provide robustness regarding noise. For example, first processing device 104 may be configured to implement linear and nonlinear observation and estimation modalities such as luenberger, kalman, sliding mode, and benes filters. The application of such observation and estimation modalities may be used to generate and infer one or more parameters associated with brain states. For example, such parameters may identify aspects of particular brain states, such as an oscillation or resonance frequency as well as a coupling and/or weighting factor associated with one or more other brain states. In a specific example, a condition of Schizophrenia may be modeled as a pair of oscillators, each being an oscillating neural pattern, and first processing device 104 may be configured to identify and determine resonance frequencies and coupling factors associated with the oscillators based on the previously described acquired measurements. In various embodiments, such coupling factors characterize coupling between individual degrees of freedom of each modeled oscillator. Accordingly, such coupling factors may be configured to identify one or more features of coupling between modeled neural oscillators, such as one or more modes.

Thus, according to various embodiments, first processing device 104 may be configured to implement direct and indirect state signature estimation. First processing device 104 may also be configured to implement brain system model parameter identification and adaptation. Furthermore, first processing device 104 may also be configured to generate an estimation of the stability of underlying hidden states, as well as noise estimation and rejection in underlying measurements. In various embodiments, first processing device 104 may also be configured to implement cognitive relevance based measurement window sizing. Accordingly, measurement windows may be sized based on cognitive relevance measures, and may be sized dynamically.

In some embodiments, first processing device 104 is configured to implement baseline estimation and removal which may enhance sensitivity regarding signatures/events. As discussed above, neural activity may be measured and represented in a time domain and/or a frequency domain. In one example, when represented in a frequency domain, the neural activity may be represented as a power spectrum that follows a plot that is logarithmic or non-linear. Accordingly, in various embodiments, first processing device 104 is configured to implement one or more curve-fitting modalities to estimate a baseline of the plot, and remove such baseline to provide a more accurate representation of more granular features of the measured signal. Such granular features may be represented with greater accuracy, and be used to identify parameters of brain states with greater accuracy.

First processing device 104 may also be configured to implement learning estimator models that learn state changes and estimate them. Such learning estimator models may also learn changing system parameters, and estimate the improvement/retrograde of behavioral/functional responses.

As similarly discussed above, observers and estimators may be used to identify and/or infer state signatures and parameters associated with brain states. For example, examples of brain state signatures may include certain lower frequency oscillations mediated with or coupled to higher frequency oscillations (delta to alpha, alpha to gamma, theta to mu, alpha to high frequency band) that correspond with various levels of cognitive ability and various types of cognitive conditions. to detect and identify signatures indicative of particular types of cognitive performance or cognitive conditions.

According to various embodiments, slow wave coupled spindle synchrony during sleep may be used as a signature of memory retention and consolidation. In particular embodiments, a closed loop control system may be configured to monitor and improve slow wave coupled spindle synchrony. In another example, first processing device 104 is configured to detect multiplexed parallel delta to theta, alpha to beta, delta/theta/alpha to high-frequency-band coupling to identify a signature of working memory. In yet another example, first processing device 104 is configured to monitor and/or control a baseline rate of exponential decay in a spectral composition of neural activity, as well as deviations from the baseline to identify and predict a cognitive and arousal state, such as an inhibitory or excitatory state. In various embodiments, first processing device 104 may also be configured to monitor beta synchronization or desynchronization to identify a signature of motor activity intent. In this way, any number of brain states and associated signature and parameters may be identified and estimated by first processing device 104. In some embodiments, first processing device 104 may be configured to identify an "activity silent" mode associated with a user in which a measure of activity is measured and tracked as a mental state shift indicator.

System 100 further includes second processing device 106 which is configured to generate functional and structural models of the brain coupled with interface 102. In various embodiments, second processing device 106 is further configured to provide brain functional model identification and adaptive learning, as well as brain structural models that model structures of the brain and are configured to implement adaptive learning. In various embodiments, second processing device 106 is communicatively coupled with interface 102, first processing device 104, as well as controller 108 discussed in greater detail below. Accordingly, second processing device 106 may receive input signals from one or more other system components and utilize such inputs to form and/or update functional and structural models of the brain coupled with interface 102. In various embodiments, second processing device 106 may also be configured to pre-process inputs received from interface 102 and first processing device 104 to generate one or more composite inputs.

In various embodiments, second processing device 106 is configured to generate functional input-output univariate and multivariate models that may be configured to approximate at least some of the input-output behavior of the brain coupled with interface 102 described above. In some embodiments, second processing device 106 is also configured to implement adaptive learning brain models that may iteratively update and improve the functional model of the brain that has been constructed.

In some embodiments, second processing device 106 is configured to implement deep/machine learning and data mining based system models. Accordingly, second processing device 106 may be configured to implement one or more artificial neural networks that may be configured to model tasks or cognitive functions of the brain. Such neural networks may be implemented in a hierarchical manner. Moreover, such neural networks may be trained based on signals received from other components of system 100. For example, models may be trained based on inputs provided to interface 102 from controller 108 and outputs measured via interface 102 as well as observers and estimators generated by first processing device 104.

In this way, input and output activity within system 100 may be used, at least in part, to construct functional and structural models represented by second processing device 106. More specifically, the artificial neural networks created by second processing device 106 may be modified and configured based on activity of the human brain. In this way, the artificial neural networks created by second processing device 106 may be specifically configured based on behaviors and processing patterns of the human mind.

In various embodiments, second processing device 106 is further configured to implement system identification, dimensional modeling, and dimension reduction to identifying preferred models. Furthermore, second processing device 106 may be configured to implement identification of one or more brain states to be controlled, as may be determined based on actuation sensitivity and efficacy. In various embodiments, second processing device 106 is configured to implement identification of the most sensitive brain states to be measured. Such identification may identify the most sensitive and granular measurement that identifies the brain state changes. In some embodiments, second processing device 106 is configured to implement multi-input, multi-output measurement and actuation. In some embodiments, second processing device 106 is further configured to multi-time scale modelling (to capture the slow system and fast system dynamic accurately). In various embodiments, second processing device 106 is also configured to implement one or more neural net basis functions that may be configured and or generated based on activity of the brain. For example, such functions may include spike functions, multi-input-coevolution triggered firing (such as coherence, synchrony, coupling, correlation of two waveforms triggering a cell firing).

While first processing device 104 and second processing device 106 have been described separately, in various embodiments, both first processing device 104 and second processing device 106 are implemented in a single processing device. Accordingly, a single processing device may be specifically configured to implement first processing device 104 and second processing device 106.

System 100 further includes controller 108 configured to implement and control closed loop control of treatments and cognitive enhancements. In various embodiments, controller 108 is communicatively coupled with interface 102, first processing device 104, and second processing device 106. Accordingly, controller 108 is configured to received inputs from various other system components, and generate outputs based, at least in part on such inputs. As will be discussed in greater detail below, such outputs may be used to provide actuations to the brain coupled with interface 102. For example, outputs generated by controller 108 may be used to stimulate the brain via one or more components of interface 102. In this way, controller 108 may provide stimuli to the brain via interface 102, may receive measurements, parameter information, and model information via other components such as first processing device 104 and second processing device 106, and may generate updated stimuli based on such received information.

Thus, according to some embodiments, controller 108 is configured to implement multi-input, multi-output feedback control. Controller 108 may also be configured to implement loop shaping optimized feedback control. In a specific example, controller 108 is configured to implement model reference adaptive control. Furthermore, controller 108 may be configured to implement cognitive enhancement trajectory control. In various embodiments, controller 108 is configured to implement enhanced control in which one or more parameters of a treatment may be enhanced by increasing its efficiency and/or effect. For example, an input or stimulation may be reduced to implement a same enhancement, a duration of stimulations may be reduced but still reach desired improvement, and a path of recovery may be made more efficient. In this way, an amount of stimulation, which may be a combination of amplitude and duration, may be reduced while still obtaining a desired effect, thus increasing the efficacy of the treatment and reducing overstimulation. In various embodiments, controller 108 is configured to implement a genetic algorithm to identify a particular stimulation pathway that reduces an amount of stimulation.

In some embodiments, controller 108 is configured to implement combined control of pharmacological and stimulation inputs. Accordingly, controller 108 may be configured to modify stimulation inputs based on an expected effect of one or more pharmacological agents that may be administered in conjunction with the stimulation. In this way, controller 108 may modify and control administration of stimuli via interface 102 based on an identified pharmacological regimen. In various embodiments, controller 108 is configured to implement game theoretic strategy-based treatments. In some embodiments, controller 108 is configured to implement real time measurement/estimation and control.

In various embodiments, controller 108 is configured to receive a reference signal which may be used, at least in part, to generate or modify the stimuli provided via interface 102. In various embodiments, the reference signal may be a previously determined signal or pattern that may represent a reference level or pattern of neural activity. In some embodiments, the reference signal may be generated based on a "negative" model. In a specific example, such a negative model may be a functional and/or structural model that is generated based on a reverse or inversion of one or more of the models created and stored by second processing device 106. Accordingly, such a negative model may be generated by second processing device 106, and the reference signal may be generated by second processing device 106 and received at controller 108.

As will be discussed in greater detail below, the above-described components of system 100 may be specifically configured to provide one or more particular applications. For example, system 100 may be configured to provide bio-signal interpretation for status monitoring and diagnostics. Accordingly, the brain state information observed and derived by at least first processing device 104 and second processing device 106 may be used to identify brain states, the onset of particular brain states, and particular transitions between brain states. Such events may be detected, and notifications may be generated by, for example, controller 108. Such notifications may be provided to other entities that may be involved in status monitoring and diagnostics, such as computing and mobile devices associated with medical professionals, or a user's in-home medical system.

Moreover, system 100 may be configured to provide augmented reality (AR)-virtual reality (VR) for cognitive enhancements and side-effect removal. For example, brain state and associated parameter detection may be used to identify the onset of particular cognitive states, such as motion sickness. When detected, or even when the onset is detected, controller 108 may generate one or more stimuli, which may be visual stimuli, tactile stimuli, and/or electric stimuli, to alleviate the detected cognitive state. In this way, motion sickness associated with VR may be alleviated.

In various embodiments, system 100 is configured to provide cognitive and behavioral modulation specific to a particular psychological or neurophysiological condition. For example, a condition such as depression may be characterized by a frozen brain state, or a brain state that does not oscillate as a normal brain would. In various embodiments, system 100 may be configured to identify a particular brain state, identify that it is "frozen" (has not changed over a designated period of time), and generate one or more control signals that are configured to stimulate the user's brain and change the brain state of the user by virtue of the stimulation to alleviate the depression. In another example, such generation of control signals may be used to alleviate or manage pain, as may be applicable with chronic pain. Such control signals associated with pain management may be implemented using multi-modal (multi-sensory) stimulation. In yet another example, generation of control signals may be utilized for stimulation based reversal of 'minimally-conscious' or 'comatose' brain states of users.

In some embodiments, system 100 may be configured to provide system and pathology specific functional brain models, as may be utilized in pharmacological applications. Accordingly, as discussed above, the use of pharmacological agents may be identified, and models may be updated in response to such pharmacological agents being identified. In this way, administration of stimuli via interface 102 may be modified and updated based on the application of a pharmacological agent to a user. More specifically, such modifications may be implemented based on the identification of the use of pharmacological agents, as well as directly measured neural activity of the user during the treatment process.

In another example, system 100 may be configured to provide model based adaptive control paradigms for feedback treatments and cognitive enhancements. Accordingly, as discussed above, treatments and cognitive enhancements may be provided with adaptive closed loop control that enables the modification and updating of such treatments and cognitive enhancements based on directly measured neural activity over the course of the treatments and cognitive enhancements.

In various embodiments, system 100 may be configured to provide smart embedded prosthetics (e.g. speech decoder, motor control). Accordingly, signals generated by controller 108 may be used to control one or more embedded prosthetics, such as prosthetic 112. In some embodiments, prosthetic 112 may be an implanted stimulator that may be activated by controller 108 in response to the detection or identification of one or more brain states or parameters associated with such brain states. In a specific example, prosthetic 112 may be a stimulator configured to prevent epileptic episodes. In this example, controller 108 may identify a brain state corresponding to an onset of an epileptic seizure, and may provide a signal to prosthetic 112 that activates prosthetic 112 to prevent the seizure.

In some embodiments, system 100 may be configured to provide a toolbox configured to support estimation, modeling, and control. In another example, system 100 may be configured to provide a bio operating system (BoS) framework for biological measurement and an actuation control platform. In some embodiments, system 100 may be configured to provide task specific cognitive enhancements, such as FAA monitoring agents, and fighter pilot related tasks.

System 100 and its respective components may be implemented in a variety of contexts. For example, system 100 may be implemented in a clinical setting that may include an examination room, an operating room, or an emergency room. Moreover, system 100 may be implemented in a user's home thus providing in-home monitoring, diagnostic, and treatment. Furthermore, portions of system 100 may be implemented in a first location while other portions are implemented in a second location. For example, interface 102 may be located at a user's home, while first processing device 104, second processing device 106, and controller 108 are implemented remotely, as may be the case when implemented at a hospital.

Furthermore, system 100 may be implemented across multiple users. For example, system 100 may include multiple interfaces that are coupled with multiple brains. In this way, measurements may be made from multiple users, and stimuli may be provided to multiple users. In one example, measurements from a first user may be used to generate and provide stimuli to a second user. In this way, synchronization of at least part of a brain state may be implemented across multiple users.

Figure 2:
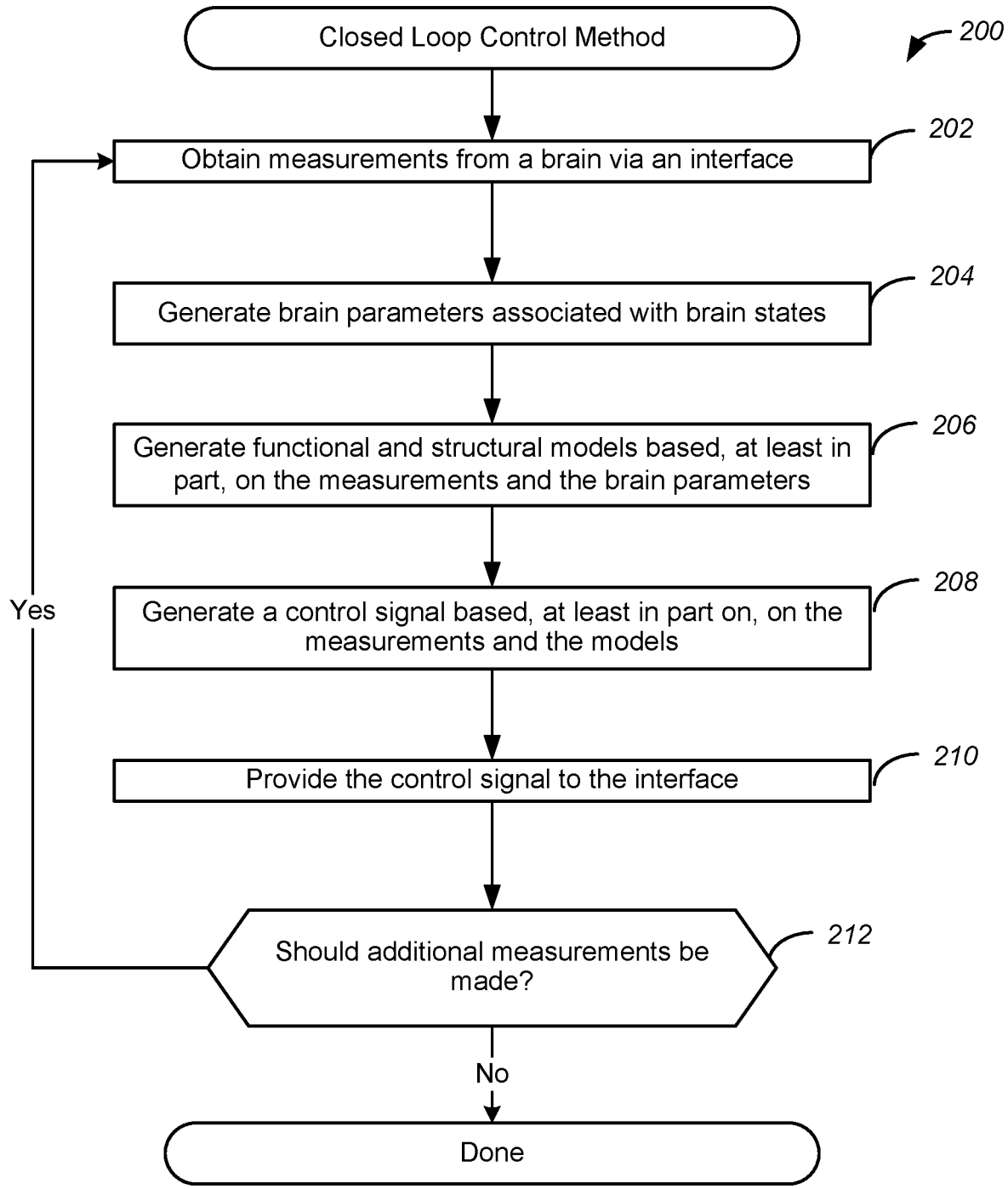
FIG. 2 illustrates an example an example of a flow chart of a method for providing closed loop control in treatments and cognitive enhancements, implemented in accordance with some embodiments.

FIG. 2 illustrates an example an example of a flow chart of a method for providing closed loop control in treatments and cognitive enhancements, implemented in accordance with some embodiments. As discussed above, various components of system 100 may be configured to implement modeling and closed loop management of treatments and therapies provided to a user.

Accordingly, method 200 may commence with operation 202 during which measurements are obtained from a brain via an interface. The measurements may represent neural activity over a particular period of time, or temporal window, and may be obtained via components of a brain interface. Such measurements may be acquired and stored in a memory.

Method 200 may proceed to operation 204 during which parameters associated with brain states are generated. As similarly discussed above, such parameters may include observers and estimators associated with brain states as well as identification of the brain states themselves. Such parameters may be generated by a first processing device and may be stored in a local memory.

Method 200 may proceed to operation 206 during which functional and structural models are generated based, at least in part, on the measurements and the parameters. As discussed above, such models may emulate functions, tasks, and components of the user's brain, and may be configured based on the brain's activity and behavior. Such models may also be configured based on previously obtained reference data.

Method 200 may proceed to operation 208 during which a control signal is generated based, at least in part on, on the measurements and the models. Accordingly, one or more control signals may be generated based on recent neural activity represented by measurement data, and also based on expected or desired effects as determined based on the models. In this way, specific control signals may be generated to implement a particular cognitive modulation that is specifically configured for the user. Moreover, as discussed above and in greater detail below, such control signals may be generated and implemented in a closed loop manner.

Method 200 may proceed to operation 210 during which the control signal is provided to the interface. Accordingly, the control signal may be provided to the interface which may generate one or more stimuli based on the control signal. For example, such stimuli may include electrical stimuli, visual stimuli, aural stimuli, and/or tactile stimuli that may have parameters, such as amplitude and duration, determined based on the control signal.

Method 200 may proceed to operation 212 during which it may be determined if additional measurements should be made. In various embodiments, such a determination may be made based on a current state, or in response to one or more conditions. For example, if a particular therapeutic regimen is implemented, a series of measurement may be made according to a predetermined schedule, and such measurements may be stepped through utilizing a state machine. If it is determined that additional measurements should be made, method 200 may return to operation 202. If it is determined that no additional measurements should be made, method 200 may terminate.

Figure 3:
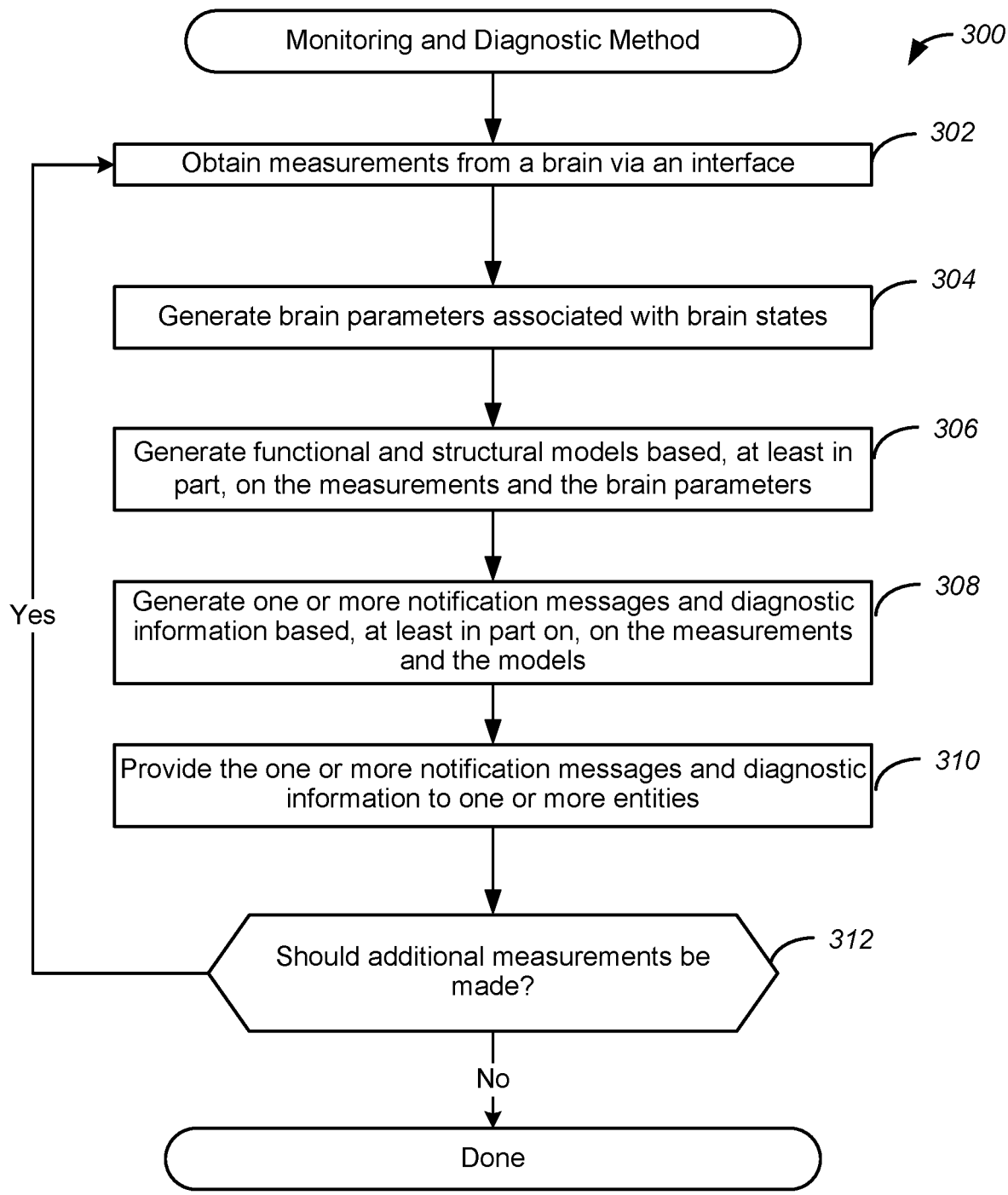
FIG. 3 illustrates an example of a flow chart of a method for status monitoring and diagnostics, implemented in accordance with some embodiments.

FIG. 3 illustrates an example of a flow chart of a method for status monitoring and diagnostics, implemented in accordance with some embodiments. As discussed above, various components of system 100 may be configured to identify particular brain states of a user based on the measured neural activity of a user, and may be further configured to generate notification messages or other status monitoring and diagnostic information.

Method 300 may commence with operation 302 during which measurements are obtained from a brain via an interface. As similarly discussed above, such measurements may represent neural activity over a particular period of time, or temporal window, and may be obtained via components of a brain interface. In various embodiments, the neural activity may be associated with a particular cognitive or therapeutic condition, and the acquisition of such measurements may be implemented responsive to detection of an event or one or more other conditions.

Method 300 may proceed to operation 304 during which parameters associated with brain states are generated. As similarly discussed above, such parameters may include observers and estimators associated with brain states as well as identification of the brain states themselves. As also discussed above, such parameters may be utilized to identify one or more brain states associated with a particular cognitive or therapeutic condition.

Method 300 may proceed to operation 306 during which functional and structural models are generated based, at least in part, on the measurements and the parameters. As discussed above, such models may emulate functions, tasks, and components of the user's brain, and may be configured based on the brain's activity and behavior. Such models may also be configured based on previously obtained reference data and/or previously obtained measurements.

Method 300 may proceed to operation 308 during which one or more notification messages and diagnostic information are generated based, at least in part on, on the measurements and the models. Accordingly, messages and other diagnostic information may be generated based on recent neural activity represented by measurement data and the generated models. In this way, specific identified parameters and brain states may be mapped to therapeutic conditions, or the onset of such conditions, and messages may be generated that provide one or more other entities with a notification of the occurrence of such brain states. In this way, diagnostic messages identifying the onset of particular brain states and therapeutic conditions of a user may be generated and sent to one or more other entities. As will be discussed in greater detail below, such other entities may be monitoring entities.

Accordingly, method 300 may proceed to operation 310 during which the one or more notification messages and diagnostic information are provided to one or more entities.

In various embodiments, the one or more entities may be computing devices associated with monitoring entities such as medical professionals, or a user's account. In this way, notification and diagnostic messages may be automatically generated and sent to various entities responsive to the neural activity of the user.

Method 300 may proceed to operation 312 during which during which it may be determined if additional measurements should be made. As similarly discussed above, such a determination may be made based on a current state, or in response to one or more conditions. For example, additional measurements may be made responsive to an input provided by another entity, which may be a monitoring entity, or according to a predetermined schedule. If it is determined that additional measurements should be made, method 300 may return to operation 302. If it is determined that no additional measurements should be made, method 300 may terminate.

Figure 4:
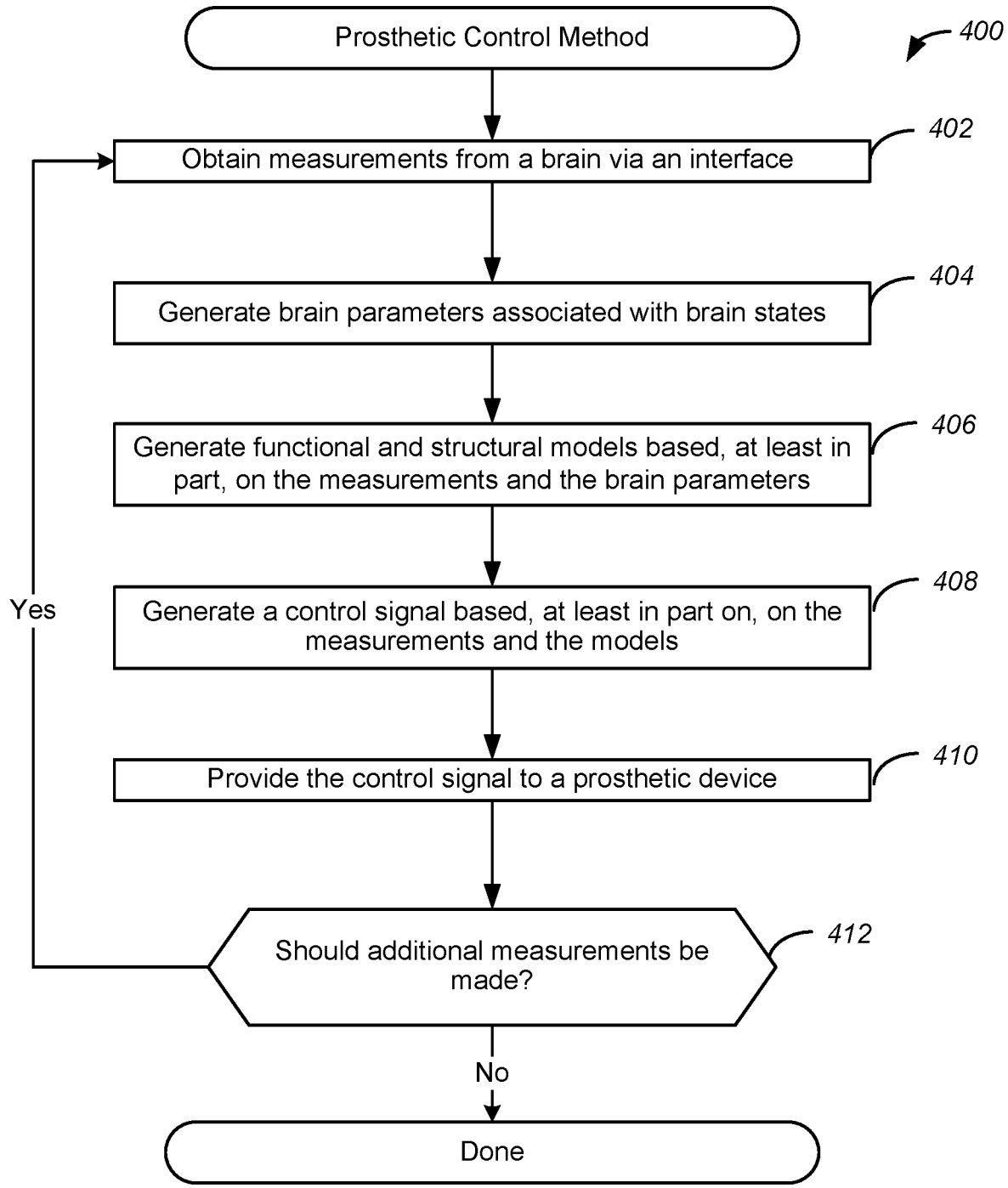
FIG. 4 illustrates an example of a flow chart of a method for control of a prosthetic, implemented in accordance with some embodiments.

FIG. 4 illustrates an example of a flow chart of a method for control of a prosthetic, implemented in accordance with some embodiments. As discussed above, various components of system 100 may be configured to control various other entities, such as prosthetics, which may be embedded prosthetics, based on the measured neural activity of a user.

Method 400 may commence with operation 402 during which measurements are obtained from a brain via an interface. As similarly discussed above, such measurements may represent neural activity over a particular period of time, or temporal window, and may be obtained via components of a brain interface. In various embodiments, the neural activity may be associated with a particular prosthetic, and the acquisition of such measurements may be implemented responsive to detection of an event or one or more other conditions.

Method 400 may proceed to operation 404 during which parameters associated with brain states are generated. As similarly discussed above, such parameters may include observers and estimators associated with brain states as well as identification of the brain states themselves. As also discussed above, such parameters may be utilized to identify one or more brain states associated with the prosthetic. As discussed above, for a prosthetic associated with epileptic seizures, parameters may be generated that may be utilized to identify brain state signatures indicative of an onset of an epileptic seizure.

Method 400 may proceed to operation 406 during which functional and structural models are generated based, at least in part, on the measurements and the parameters. As discussed above, such models may emulate functions, tasks, and components of the user's brain, and may be configured based on the brain's activity and behavior. Such models may also be configured based on previously obtained reference data and/or previously obtained measurements.

Method 400 may proceed to operation 408 during which a control signal is generated based, at least in part on, on the measurements and the models. Accordingly, one or more control signals may be generated based on recent neural activity represented by measurement data. In this way, specific control signals may be generated to implement a particular functionality of the prosthetic that is responsive to the identified brain states.

Method 400 may proceed to operation 410 during which the control signal is provided to the prosthetic. Accordingly, the control signal may be provided directly to the prosthetic from a controller, or may be provided via an interface. Moreover, the prosthetic may implement one or more operations responsive to receiving the control signal. In this way, the control signal may be implemented by the prosthetic and functionalities provided by the prosthetic may be implemented.

Method 400 may proceed to operation 412 during which it may be determined if additional measurements should be made. As similarly discussed above, such a determination may be made based on a current state, or in response to one or more conditions. For example, additional measurements may be made responsive to the activation of the prosthetic or according to a predetermined schedule. If it is determined that additional measurements should be made, method 400 may return to operation 402. If it is determined that no additional measurements should be made, method 400 may terminate.

Figure 5:
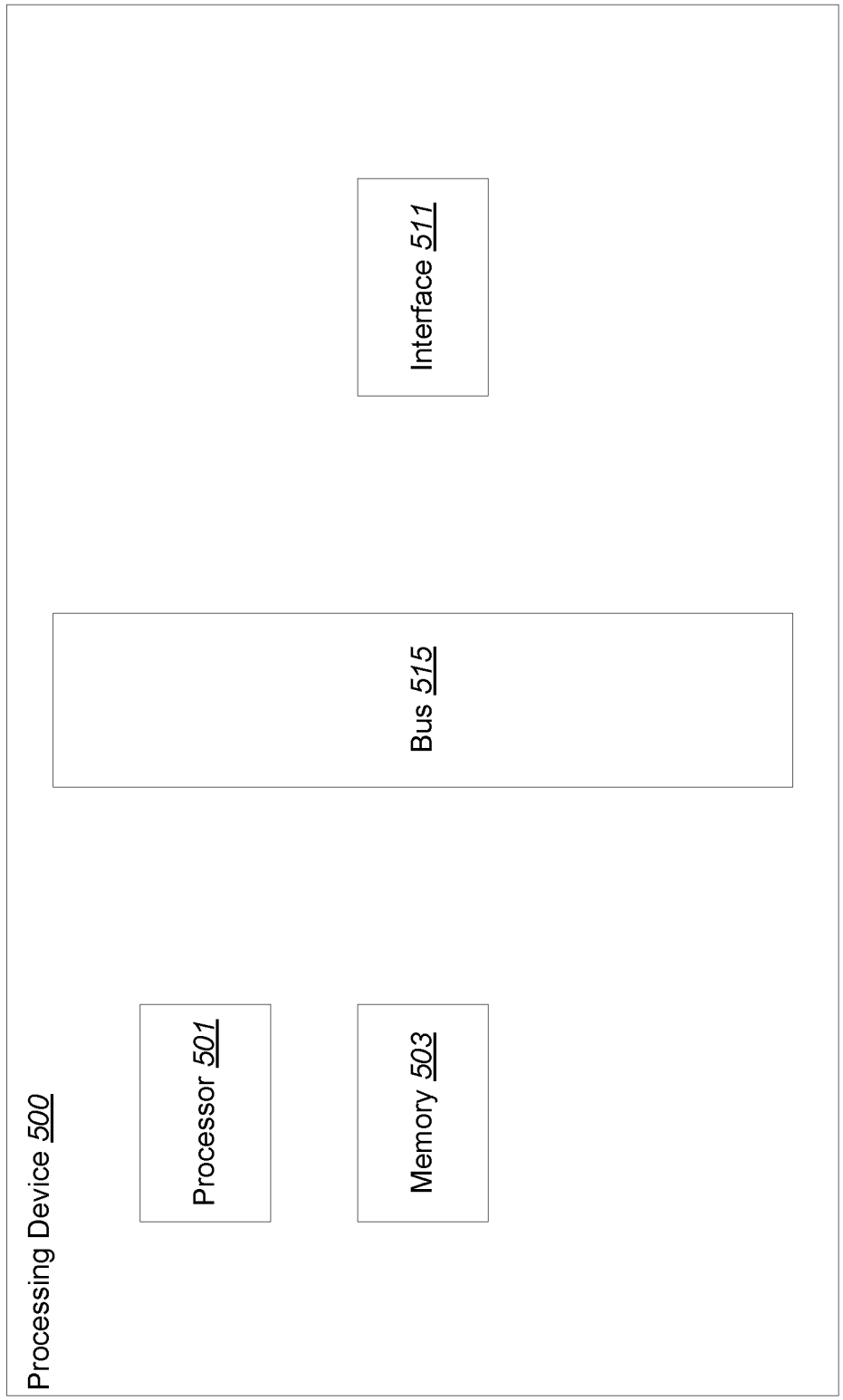
FIG. 5 illustrates an example of a processing device that can be used with various embodiments.

FIG. 5 illustrates an example of a processing device that can be used with various embodiments. For instance, the processing device 500 can be used to implement any of first processing device 104, second processing device 106, and/or controller 108 according to various embodiments described above. In addition, the processing device 500 shown can be implemented in conjunction with a computing system on a mobile device or on a computer or laptop, etc. According to particular example embodiments, a processing device 500 suitable for implementing particular embodiments of the present invention includes a processor 501, a memory 503, an interface 511, and a bus 515 (e.g., a PCI bus). The interface 511 may include separate input and output interfaces, or may be a unified interface supporting both operations. When acting under the control of appropriate software or firmware, the processor 501 is responsible for tasks such as closed loop control. Various specially configured devices can also be used in place of a processor 501 or in addition to processor 501. The complete implementation can also be done in custom hardware. The interface 511 may be configured to send and receive data packets or data segments over a network. Particular examples of interfaces the device supports include Ethernet interfaces, frame relay interfaces, cable interfaces, DSL interfaces, token ring interfaces, and the like. In various embodiments, interface 511 may also be a wired connection or a bus with appropriate communications ports.

In addition, various very high-speed interfaces may be provided such as fast Ethernet interfaces, Gigabit Ethernet interfaces, ATM interfaces, HSSI interfaces, POS interfaces, FDDI interfaces and the like. Generally, these interfaces may include ports appropriate for communication with the appropriate media. In some cases, they may also include an independent processor and, in some instances, volatile RAM. The independent processors may control such communications intensive tasks as packet switching, media control and management.

According to particular example embodiments, the processing device 500 uses memory 503 to store data and program instructions and maintain a local side cache. The program instructions may control the operation of an operating system and/or one or more applications, for example. The memory or memories may also be configured to store received metadata and batch requested metadata.

Because such information and program instructions may be employed to implement the systems/methods described herein, the present invention relates to tangible, machine readable media that include program instructions, state information, etc. for performing various operations described herein. Examples of machine-readable media include memory devices such as non-volatile memory devices, volatile memory devices, and may also utilize optical media such as CD-ROM disks and DVDs, and hardware devices that are specially configured to store and perform program instructions, such as read-only memory devices (ROM) and programmable read-only memory devices (PROMs). Examples of program instructions include both machine code, such as produced by a compiler, and files containing higher level code that may be executed by the computer using an interpreter.

While the present disclosure has been particularly shown and described with reference to specific embodiments thereof, it will be understood by those skilled in the art that changes in the form and details of the disclosed embodiments may be made without departing from the spirit or scope of the invention. Specifically, there are many alternative ways of implementing the processes, systems, and apparatuses described. It is therefore intended that the invention be interpreted to include all variations and equivalents that fall within the true spirit and scope of the present invention. Moreover, although particular features have been described as part of each example, any combination of these features or additions of other features are intended to be included within the scope of this disclosure. Accordingly, the embodiments described herein are to be considered as illustrative and not restrictive.

What is claimed is:

1. A system comprising:
   a plurality of intracranial electrodes configured to be coupled to a brain of a user and configured to obtain a plurality of measurements from the brain of the user, the plurality of measurements including an oscillation or resonance frequency;
   an interface configured to obtain the plurality of measurements from at least the plurality of intracranial electrodes;
   at least one processor configured to
   generate a plurality of brain state parameters characterizing one or more brain states of the user;
   generate at least one model of the brain of the user, using machine learning, based, at least in part, on the plurality of brain state parameters and the plurality of measurements, wherein the at least one model is configured to model input-output behavior of the brain; and
   generate a control signal based on the plurality of brain state parameters and the at least one model to obtain a desired brain state by changing the oscillation or resonance frequency.

2. The system of claim 1, wherein the plurality of measurements are intracranial measurements, and wherein each of the one or more brain states identifies a pattern of neural activity of the brain.

3. The system of claim 2, wherein the pattern of neural activity is identified based, at least in part, on brain activity at a designated frequency band, and wherein the pattern of neural activity is identified based, at least in part, on frequency oscillation and coupling factors.

4. The system of claim 2, wherein the plurality of measurements is co-registered with scalp level measurements, and wherein the plurality of brain state parameters and the at least one model are generated based on the intracranial measurements and the scalp level measurements.

5. The system of claim 2, wherein the at least one processor is further configured to generate an estimated brain state based, at least in part, on the intracranial measurements.

6. The system of claim 1, wherein the at least one model comprises a functional model of the brain and a structural model of the brain, wherein the functional model is configured to model input-output behavior of the brain, and wherein the structural model is configured to model structures of the brain.

7. The system of claim 1, wherein the the at least one processor is further configured to provide the control signal to the brain via the interface and at least one surface electrode.

8. The system of claim 7, wherein the control signal is configured to change a current brain state of the user.

9. The system of claim 1, wherein the at least one processor is configured to update the at least one model based on a plurality of additional measurements received via the plurality of electrodes.

10. The system of claim 1 wherein the at least one model comprises an artificial neural network.

11. The system of claim 1, wherein the control signal is further configured to improve slow wave coupled spindle synchrony.

12. A device comprising:
    a first processor configured to generate a plurality of brain state parameters based on a plurality of measurements received from a brain of a user, the plurality of brain state parameters characterizing one or more brain states of the user, and the plurality of measurements being intracranial measurements and including an oscillation or resonance frequency;
    a second processor configured to generate at least one model of the brain of the user based, at least in part, on the plurality of brain state parameters and the plurality of measurements; and
    a controller comprising one or more processors configured to generate a control signal based on the plurality of brain state parameters and the at least one model to change the oscillation or resonance frequency.

13. The device of claim 12, wherein each of the plurality of brain states identifies a pattern of neural activity of the brain, and wherein the pattern of neural activity is identified based, at least in part, on brain activity at a designated frequency band.

14. The device of claim 12, wherein the plurality of measurements is co-registered with scalp level measurements, and wherein the plurality of brain state parameters and the at least one model are generated based on the intracranial measurements and the scalp level measurements.

15. The device of claim 12, wherein the at least one model comprises a functional model of the brain and a structural model of the brain, wherein the functional model is configured to model input-output behavior of the brain, and wherein the structural model is configured to model structures of the brain.

16. The device of claim 12, wherein the first processor is further configured to generate an estimated brain state based, at least in part, on the intracranial measurements.

17. A method comprising:
    receiving, via an interface and a plurality of intracranial electrodes coupled to a brain of a user, a plurality of measurements from the brain of the user, the plurality of measurements being intracranial measurements and including an oscillation or resonance frequency;
    generating, using one or more processors, a plurality of brain state parameters characterizing one or more brain states of the user;
    generating, using the one or more processors, at least one model of the brain of the user, using machine learning, based, at least in part, on the plurality of brain state parameters and the plurality of measurements, wherein the at least one model is configured to model input-output behavior of the brain; and generating, using the one or more processors, a control signal based on the plurality of brain state parameters and the at least one model to obtain a desired brain state to change the oscillation or resonance frequency.

18. The method of claim 17, wherein each of the one or more brain states identifies a pattern of neural activity of the brain, and wherein the pattern of neural activity is identified based, at least in part, on brain activity at a designated frequency band.

19. The method of claim 17 further comprising:

co-registering the intracranial measurements with scalp level measurements, and wherein the plurality of brain state parameters and the at least one model are generated based on the intracranial measurements and the scalp level measurements.

20. The method of claim 17, wherein the at least one model comprises a functional model of the brain and a structural model of the brain.

21. The method of claim 17, further comprising stimulating the brain, via at least one surface electrode, based on the control signal to change a current brain state of the user.

22. The method of claim 17 further comprising:

updating the at least one model based on a plurality of additional measurements received via the plurality of electrodes.

* * * * *